United States Patent
Hopps et al.

(10) Patent No.: US 6,579,904 B1
(45) Date of Patent: Jun. 17, 2003

(54) PROCESS FOR MAKING BETAINE TRANSITION METAL COMPLEXES FOR USE IN ANIMAL FEED SUPPLEMENTS AND COMPOSITIONS THEREOF

(75) Inventors: Harvey B. Hopps, Amarillo, TX (US); Gary Culp, Amarillo, TX (US); Steven B. Malcolm, Canyon, TX (US); Ken W. Ridenour, Amarillo, TX (US); Jay Thurman, Canyon, TX (US)

(73) Assignee: K.E.R. Associates, Inc., Amarillo, TX (US)

( * ) Notice: Subject to any disclaimer, the term of this patent is extended or adjusted under 35 U.S.C. 154(b) by 203 days.

(21) Appl. No.: 09/668,618

(22) Filed: Sep. 22, 2000

(51) Int. Cl.$^7$ ................................................ A01N 55/02

(52) U.S. Cl. ........................ 514/492; 514/494; 514/499; 514/501; 514/502; 514/505; 556/50; 556/64; 556/116; 556/134; 556/148; 424/442

(58) Field of Search ........................... 556/50, 64, 134, 556/116, 148; 514/492, 494, 499, 501, 502, 505; 424/442

(56) References Cited

U.S. PATENT DOCUMENTS

| | | | |
|---|---|---|---|
| 2,800,502 A | 7/1957 | Vassel | 260/501 |
| 3,463,858 A | 8/1969 | Anderson | 424/289 |
| 3,925,433 A | 12/1975 | Abdel-Monem et al. | 260/438 |
| 3,941,818 A | 3/1976 | Abdel-Monem | 260/429.9 |
| 3,950,372 A | 4/1976 | Abdel-Monem | 260/429 R |
| 4,021,569 A | 5/1977 | Abdel-Monem | 424/289 |
| 4,039,681 A | 8/1977 | Abdel-Monem | 424/289 |
| 4,067,994 A | 1/1978 | Anderson et al. | 424/295 |
| 4,485,261 A | 11/1984 | Ashina et al. | 564/479 |
| 4,670,269 A | 6/1987 | Abdel-Monem | 426/74 |
| 4,678,854 A | 7/1987 | Abdel-Monem | 556/149 |
| 4,764,633 A | 8/1988 | Anderson et al. | 556/50 |
| 4,900,561 A | 2/1990 | Abdel-Monem et al. | 426/2 |
| 4,956,188 A | 9/1990 | Anderson | 426/74 |
| 4,980,353 A | 12/1990 | Grohe et al. | 514/254 |
| 4,981,854 A | 1/1991 | Grohe et al. | 514/254 |
| 4,990,517 A | 2/1991 | Petersen et al. | 514/300 |
| 5,075,498 A | 12/1991 | Perine et al. | 562/575 |
| 5,081,293 A | 1/1992 | Borland et al. | 562/575 |
| 5,105,008 A | 4/1992 | Sauer et al. | 562/575 |
| 5,120,873 A | 6/1992 | Perine et al. | 562/575 |
| 5,292,538 A | 3/1994 | Paul et al. | 426/74 |
| 5,292,942 A | 3/1994 | Aigner et al. | 562/575 |
| 5,371,250 A | 12/1994 | Seitz et al. | 554/70 |
| 5,464,565 A | 11/1995 | Hamann et al. | 252/546 |
| 5,571,527 A | 11/1996 | Nishimura et al. | 424/438 |
| 5,583,243 A | 12/1996 | Abdel-Monem | 556/149 |
| 5,633,004 A | 5/1997 | Nishimura et al. | 424/438 |
| 5,635,198 A | 6/1997 | Nishimura et al. | 424/438 |
| 5,681,972 A | 10/1997 | Hamann et al. | 554/69 |
| 5,684,191 A | 11/1997 | Bellis et al. | 562/575 |
| 5,696,287 A | 12/1997 | Bellis | 562/575 |
| 5,698,724 A | 12/1997 | Anderson et al. | 556/50 |
| 5,885,610 A | 3/1999 | Anderson | 424/438 |
| 5,895,823 A | 4/1999 | Ramprasad et al. | 562/575 |
| 5,962,708 A | 10/1999 | Hamann et al. | 554/69 |
| 5,962,709 A | 10/1999 | Uphues et al. | 554/70 |
| 6,034,216 A | 3/2000 | Somers et al. | 530/331 |

FOREIGN PATENT DOCUMENTS

| | | |
|---|---|---|
| EP | 0891719 A1 | 1/1999 |
| WO | WO 96/36598 | 11/1996 |
| WO | WO 99/63943 | 12/1999 |

OTHER PUBLICATIONS

Chen et al., Inorganica Chimica Acta, vol. 182, pp. 139–144 (1991).*

Chen et al., Polyhedron, vol. 10, No. 2, pp. 273–276 (1991).*

Chemical Abstracts No. 123144627:123(11) 144627r. "Synthetic Method of Betainem" by Changmao Hong et al. Based on CN1084505A, Mar. 30, 1994.

Abstract 169, "Carcass and Performance Responses to Feeding Betaine in Pigs," by K.R. Cera et al., *J. Anim. Sci.*, vol. 73, Suppl. 1, p. 82 (1995).

Abstract 170, "The Effects of Betaine Supplementation on Growth Performance and Carcass Characteristics in Finishing Pigs," by D.M. Webel, et al., *J. Anim. Sci.*, vol. 73, Suppl. 1, p. 82 (1995).

Abstract 171, "Interrelationships Between Dictary Methionine and Betaine on the Growth Performance of Pigs from 65 to 100 kg," by R.G. Campbell, et al., *J. Anim. Sci.*, vol. 73, Suppl. 1, p. 82 (1995).

Abstract 172, "Effect of Dietary Betaine Additions and Amino: Calorie Ratio on Performance and Carcass Traits of Finishing Pigs," by K.D. Haydon, et al., *J. Anim. Sci.*, vol. 73, Suppl. 1, p. 82 (1995).

Abstract 173, "The Effects of Supplementing Growing Finishing Swine Diets with Betaine and (or) Choline on Growth and Carcass Characteristics," by J.W. Smith, et al., *J. Anim. Sci.*, vol. 73, Suppl. 1, p. 83 (1995).

Abstract 340, "Performance of Pigs Fed Betaine from 60 to 110 kg Body Weight," by B.V. Lawrence, et al., *J. Anim. Sci.*, vol. 73, Suppl. 1, p. 195 (1995).

Abstract 341, "Effects of Betaine (Betafin–BCR) on Growth and Carcass Characteristics of Finishing Pigs," by J.O. Matthews, et al., *J. Anim. Sci.*, vol. 73, Suppl. 1, p. 82 (1995).

(List continued on next page.)

*Primary Examiner*—Porfirio Nazario-Gonzalez
(74) *Attorney, Agent, or Firm*—Floyd Nation; Carter White; Howrey Simon Arnold & White, LLP

(57) ABSTRACT

Betaine transition metal complexes are formed by: a) reacting a solution including an alkali metal salt of chloroacetic acid with a solution including the transition metal salt to give a solution including a chloroacetate transition metal complex; and b) reacting the solution including the chloroacetate transition metal complex with trimethylamine to give a solution including the betaine transition metal complex. Such betaine transition metal complexes may be used as a feed supplement for animals in the process of preparing such animals for market.

25 Claims, No Drawings

OTHER PUBLICATIONS

Abstract 1054, "The Effects of Dictary Carnitine, Betaine and Chromium Nicotinate Supplementation on Growth and Carcass Characteristics in Growing–Finishing Pigs," by J.W. Smith, et al., *J. Anim. Sci.*, vol. 72, Suppl. 1, p. 274 (1994).

Abstract 258, "The Role of Methionine as a Methyl Group Donor in Cattle," by C.A. Loest, et al., *J. Anim. Sci.*, vol. 77, Suppl. 1, p. 85.

Abstract 602, "Effects of Dietary Protein and Ruminally Protected Betaine or Choline on Productivity of Angora Doelings," by R. Puchala, et al., *J. Anim. Sci.*, vol. 73, Suppl. 1, p. 261.

Article "Betaine's Benefits in Poultry Production," by Philip Lobo, *Feed Management*, vol. 50, No. 10, pp. 13–16, Dec. 1999.

Chapter 3, "Betaine in Animal Metabolism," *The Betafin Briefing*, vol. 1, Finsugar 3ioproducts, pp. 17–29.

Section 1201, "Betaine," *The Merck Index*, pp. 183–184 (1989).

Article "Review Compares Use of Betaine as Methionine Replacement for Poultry," by William A. Dudley–Cash.

Article "Betaine as a Dietary Supplement For Finishing Cattle," by C.A. Loest, et al. *Cattlemen's Day*, pp. 76–78 (1998).

Article "The Influence of Betaine on Untrained and Trained Horses Exercising to Fatigue," by L. K. Warren, et al., *J. Anim. Sci.*, vol. 77, pp. 677–684 (1999).

Article "Interactive Effects of Betaine, Momensin in Chicks Reported," by William A. Dudley–Cash, *Feedstuffs*, Aug. 4, 1997.

Article "Hepatic and Renal Betaine–Homocysteine Methyltransferase Activity in Pigs as Affected by Dietary Intakes of Sulfur Amino Acide, Choline, and Betaine," by Jason L. Emmert, et al., *J. Anim. Sci.*, vol. 76, pp. 606–610 (1998).

Article "Can Betafin Spare Methionine," by Luisa Rosi, *Betafin News*.

Article "Betaine and Carnitine," by Jack Odle, *Feed Management*, vol. 47, No. 1, Jan. 1996.

Article Effect of Trimethylamine Oxide and Betaine in Swine Diets on Growth Performance, Carcass Characteristics, Nutrient Digestibility, and Sensory Quality of Pork, 'by M. Overland, et al. *J. Anim. Sci.*, vol. 77, pp. 2143–2153 (1999).

Article "Can Betaine Replace Supplemental DL–Methionine in Broiler Diets," by H.S. Rostagno, et al., *J. of Applied Poultry Research*, vol. 5, No. 2 (1996).

\* cited by examiner

PROCESS FOR MAKING BETAINE TRANSITION METAL COMPLEXES FOR USE IN ANIMAL FEED SUPPLEMENTS AND COMPOSITIONS THEREOF

BACKGROUND OF THE INVENTION

The present invention relates to a method of making a betaine transition metal complex, and the use and compositions including the betaine transition metal complex as a feed supplement for animals.

Due to efforts to supply food to a growing population of consumers, it has become common practice to supplement the feed of livestock and poultry with additives to stimulate growth, retard disease, and to achieve other such desirable results. Common agents administered to animals as feed supplements include antibiotics, vitamins, amino acids and trace minerals such as zinc, chromium, manganese, iron, cobalt and copper.

Betaine can potentially be beneficial to livestock if administered as a feed supplement. Betaine can act as a methyl donor, a metabolic role that is typically performed by two other important nutrients: methionine and choline. By relieving these two nutrients of their methyl donating duties, betaine can spare methionine and choline to perform other important physiological functions, thus increasing growth in the animal. Betaine also plays a role in osmotic regulation and stabilizes cellular metabolism. These functions help the animal adapt to environmental stress. Betaine has been explored as a feed additive for poultry and swine, but thus far has not been extensively studied for use in cattle.

One consideration in designing a betaine food supplement is bio-availability. To be effective, a food supplement must deliver the intended agent in a bio-available form. This is sometimes problematic. For example, bacteria in the rumen of cattle can degrade amino acid sources like lysine and methionine before the sources have time to pass from the rumen to the small intestine where they can be absorbed. Thus, the amino acids are not bio-available and therefore the animal does not reap the benefit of the supplement. Likewise, it is known that trace minerals in the form of inorganic salts are not readily absorbed in the gut of many animals. In natural food sources these minerals are usually present as coordination complexes. However, simply complexing the minerals with complexing agents such as ethylenediaminetetraacetate (EDTA) does not solve the problem because the complexes are so stable that they are readily excreted rather than absorbed. To be bio-available, a complex must have an intermediate stability so that it can withstand the conditions of the gastrointestinal tract and can also be absorbed by the animal.

One method of delivering bio-available trace minerals and amino acids to live stock is to form a complex of the amino acid and the trace mineral. For example, the essential amino acid methionine has been used to provide a bio-available amino acid-trace mineral complex supplement with trace minerals such as zinc, chromium, manganese, magnesium, copper, cobalt, and iron.

Another consideration in developing a betaine food supplement is its synthesis. Betaine is typically prepared by the reaction of a haloalkanoate salt with excess trimethylamine. A drawback to this process is that the product is often contaminated with unreacted starting materials, particularly trimethylamine, which is difficult to remove.

Furthermore, free betaine is not the most ideal form of betaine to use as a feed supplement, particularly if the intended recipient animal is a ruminant. As with lysine and methionine mentioned above, bacteria in the rumen can degrade betaine before it can be absorbed in the intestine. It would be highly desirable to have a synthetic method yielding betaine in a highly bio-available form and not requiring difficult purification of the product.

SUMMARY OF THE INVENTION

The present invention is generally directed to a method of making a betaine transition metal complex, and the use and compositions including the betaine transition metal complex as a feed supplement for animals. The inventive method includes the steps of: a) reacting a solution including an alkali metal salt of chloroacetic acid with a solution including the transition metal salt to give a solution including a chloroacetate transition metal complex; and b) reacting the solution including the chloroacetate transition metal complex with trimethylamine to give a solution including the betaine transition metal complex. The inventive method may be carried out such that reacting chloroacetic acid with a neutralizing amount of alkali metal hydroxide to give the alkali metal salt of chloroacetic acid generates the alkali metal salt of chloroacetic acid. In one preferred embodiment of the inventive method, the transition metal salt is selected from zinc salts, copper salts, iron salts, chromium salts, manganese salts, cobalt salts, their hydrates and mixtures of these salts, and in a more preferred method the transition metal salt is selected from zinc halide salts, zinc sulfate salts, zinc nitrate salts, copper halide, copper sulfate copper nitrate, iron halide, iron sulfate, iron nitrate, chromium halide, chromium sulfate, chromium nitrate, manganese halide, manganese sulfate, manganese nitrate, cobalt halide, cobalt sulfate, cobalt nitrate, the hydrates of these salts and the mixture of these salts. In another embodiment, the transition metal salt is a zinc salt, and preferably the zinc salt is selected from zinc chloride, zinc bromide, zinc sulfate, zinc nitrate, their hydrates and combinations of these. The reactions of the method may take place in any suitable solvent, but preferably the reactions take place in an aqueous solvent. The inventive method may further include the step of stripping any excess trimethylamine from the solution including the betaine transition metal complex. The isolation of the betaine transition metal complex may also be included as a step within the inventive method in which case the process would include the step of isolating the betaine transition metal complex by precipitation or evaporative reduction of the solution including the betaine transition metal complex.

The product of the inventive method is a betaine transition metal betaine complex salt having the formula

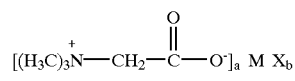

wherein a is a value between 1 and 6; M is a transition metal ion selected from zinc, copper, iron, chromium, manganese, cobalt and mixtures thereof; X is a counter ion and b is a whole integer selected to electrostatically balance the charge of the complex salt. Within such an illustrative embodiment, it is preferred that the counter ion X is selected from halide, sulfate, nitrate and mixtures thereof. Further the transition metal ion may be selected from zinc (II), copper (II), copper (I), iron (II), iron (III), cobalt (II), cobalt (III), chromium (II), chromium (III), manganese (II) manganese (III), and mixtures of these. Preferably the transition metal ion M is zinc and the counter ion X is a halide, sulfate or other similar suitable counter ion. As indicated the value of a may have a value from 1 upto and including 6, but preferably the value of a is 2 to 4.

Another embodiment of the present invention is a trace metal feed supplement comprising an effective amount of the transition metal betaine complex that is preferably the product of the above described process. The illustrative trace metal feed supplement may be delivered as a solution, preferably an aqueous solution, or it may be delivered in solid form. The solid form may include a carrier such as animal feed, rice hulls, or other suitable carrier for feed supplements.

One of skill in the art should also appreciate that the present invention also includes other related aspects such as a method for providing the above described trace metal-betaine feed supplement to an animal. Such a method includes the steps: a) mixing a suitable animal feed mixture with an effective amount of a trace metal betaine complex, and b) providing said supplemented feed mixture to the animal for consumption by the animal. An additional aspect of the present invention is the animal feed composition itself which includes: an effective amount of a trace metal betaine described herein and a suitable animal feed mixture for said animal. The present invention also should be understood to include a method of making an animal feed composition including mixing an effective amount of a trace metal betaine complex salt with a suitable animal feed mixture for said animal to form said animal feed mixture.

These and other features of the present invention are more fully set forth in the following description of illustrative embodiments of the invention.

DESCRIPTION OF ILLUSTRATIVE EMBODIMENTS

According to one aspect of the present invention, a betaine transition metal complex is made by: a) reacting a solution of an alkali metal salt of chloroacetic acid with a solution including the transition metal salt to give a solution including a chloroacetate transition metal complex; and b) reacting the solution including the chloroacetate transition metal complex with trimethylamine to give a solution including the betaine transition metal complex.

In accordance with the teachings of the present invention, the first step in the synthesis of the transition metal betaine complexes disclosed herein is the dissolution of chloroacetic acid in an appropriate solvent. Suitable solvents include water, methanol, ethanol, diethyl ether, ethyl acetate, tetrahydrofuran and other polar solvents. A particularly suitable solvent is water. The pH of the solution should be raised to deprotonate the chloroacetic acid to form chloroacetate ion in solution. The resulting pH of the solution may preferably be from about 3.0 to about 13.0, more preferably from about 5.0 to about 10.0 and most preferably from about 7.8 to about 9.0. The pH of the solution should be raised by the addition of a neutralizing amount of a basic solution. Suitable bases include hydroxides of alkali metals, rare earth metals, ammonia and quaternary amines, protonated tertiary amines and other compounds that may neutralize chloroacetic acid. Particularly suitable bases are sodium hydroxide and potassium hydroxide. The temperature of the solution should be maintained between the freezing point and up to and including the boiling point of the solution at ambient pressure. Preferably the temperature of the solution may be maintained below the boiling point of the solution, and most preferably the solution is maintained at or about that of the ambient room temperature. A solution of the metal salt may then be added to the solution of the chloroacetate although the order of addition is not critical. However, one of skill in the art of forming transition metal complexes should understand and appreciate that it is preferable to add the transition metal to the solution containing the complexing agent as opposed to the opposite.

In one preferred embodiment of the illustrative method, the metal salt may be a transition metal of the first row. More preferably the transition metal is one or more selected from zinc salts, copper salts, iron salts, chromium salts, manganese salts, cobalt salts, their hydrates and mixtures of these salts. One of skill in the art should appreciate that the selection of the transition metal may have differing effects on the nutritional aspects of the present invention. In a more preferred illustrative method the transition metal salt is selected from zinc halide salts, zinc sulfate salts, zinc nitrate salts, copper halide, copper sulfate copper nitrate, iron halide, iron sulfate, iron nitrate, chromium halide, chromium sulfate, chromium nitrate, manganese halide, manganese sulfate, manganese nitrate, cobalt halide, cobalt sulfate, cobalt nitrate, the hydrates of these salts and the mixture of these salts. In another illustrative embodiment, the transition metal salt is a zinc salt, and preferably the zinc salt is selected from zinc chloride, zinc bromide, zinc sulfate, zinc nitrate, their hydrates and combinations of these.

In the second step of the present illustrative method, trimethylamine may be then added to the solution of chloroacetate-metal complex to yield the betaine-metal complex. Trimethylamine can be added as a solution of trimethylamine in an appropriate solvent, or alternatively, it may be added as a gas. The amount added should be sufficient to react with the chloroacetate metal complex to form the betaine complex. In one preferred embodiment the amount of trimethylamine added is a slight molar excess of the chloroacetate content transition metal complex. According to a preferred embodiment of the present invention, trimethylamine is added as an aqueous solution that is about 25% in trimethylamine. The resulting solution is stirred for a time ranging from 0.5 to about 24 hours so as to allow the reaction to come to a point of completion. Preferably the reaction mixture is stirred for about 5 minutes to about 90 minutes and more preferably from about 15 minutes to about 30 minutes. Excess trimethylamine is then removed from the reaction mixture by sparging with an inert gas such as nitrogen, distillation, extraction or other suitable method. According to one embodiment of the present invention, excess trimethylamine is removed from the reacting mixture by distillation. Another preferred method of isolating the betaine-transition metal complex includes the evaporative reduction of the solution, which results in the precipitation and isolation of the betaine transition metal complex.

In addition to the above method, the present invention is directed to the product of the above-described method. That is to say, the present invention also encompasses transition metal complexes of betaine. Such a metal complex should have the general formula:

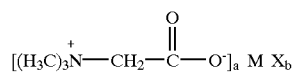

wherein a is a value between 1 and 6 and M is a transition metal ion selected from the first row transition metals and preferably zinc, copper, iron, chromium, manganese cobalt and mixtures thereof. In order to achieve electrostatic balance, X serves as a counter ion and b is a whole integer selected to electrostatically balance the charge of the complex salt. Within such an illustrative embodiment, it is preferred that the counter ion X may be selected from any suitable counter ion, but preferably may be selected from halide, sulfate, nitrate and mixtures thereof. In a more preferred illustrative embodiment, the transition metal ion may be selected from zinc (II), copper (II), copper (I), iron (II), iron (III), cobalt (II), cobalt (III), chromium (II), chromium (III), manganese (II) manganese (III), and mixtures of these. Optimally, the transition metal ion M is zinc and the counter ion X is a halide, sulfate or other similar suitable counter ion. As indicated the value of a may have a nominal value from 1 upto and including 6, but preferably the value of a is 2 to 4. The exact value will depend upon the selection of the metal ion, the condition under which the complex is formed and the potential for the formation of other more stable complexes. Such factors in the formation of transition metal complexes should be known to one of ordinary skill in the art and the determination of the exact value for a is not necessarily critical to the functioning of the present invention.

Another illustrative embodiment of the present invention is a trace metal feed supplement comprising an effective amount of the transition metal betaine complex that is preferably the product of the above described process. The illustrative trace metal feed supplement may be delivered as a solution, preferably an aqueous solution, or it may be delivered in solid form. The solid form may be made by the combination of the transition metal betaine complex with a suitable carrier. Such suitable carriers may include a suitable animal feed for the target animal, rice hulls, cracked grains such as cracked corn, cracked wheat, cracked barley and the like or other suitable carrier for feed supplements.

Also within the scope of the present invention is a method of enhancing the growth of animals by supplementing the animal feed with the transition metal betaine complexes of the present invention. In such a method an effective amount of the transition metal betaine complexes of the present invention are fed to animals in order to enhance growth and market value. Typically, in such an embodiment, the transition metal betaine complex is mixed, sprayed, or otherwise included in the feed provided to the animal in preparation of the animal for market. One of ordinary skill in the art of animal husbandry should be able by empirical methods to determine the optimum amount of betaine transition metal complex that should be added to the feed to achieve the desired results. Care and professional judgement should be used in determining the amount of transition metal betaine complex to be fed a particular animal so as to avoid any deleterious effects on the animal. The transition metal betaine complexes of the present invention may be sprayed onto the feed or a suitable carrier may be used to enhance the ability to handle and mix the feed. For example, suitable carriers may include rice hulls, cracked grains such as cracked corn, cracked wheat, cracked barley and the like or other suitable carriers for feed supplements.

The following examples are included to demonstrate embodiments of the invention for the formation of the transition metal betaine complex. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLE 1.

Chloroacetic acid (0.01 mol.) was dissolved into distilled water (250 ml). Sodium hydroxide (0.25 M) was added until the pH of the solution reached 8.4, thus yielding the sodium salt of chloroacetic acid (sodium chloroacetate) in situ. An aqueous solution of zinc chloride was added dropwise until 0.01 moles had been added, thus yielding the metal-chloroacetate compound in situ. Trimethylamine solution (25%, aqueous) was added until a total of 0.01 moles had been added. The solution was allowed to stir for about 15 to about 30 minutes at 25° C., thus yielding a betaine-metal complex as the final product.

EXAMPLE 2.

Chloroacetic acid (0.01 mol.) was dissolved into distilled water (250 ml). Sodium hydroxide (0.25 M) was added until the pH of the solution reached 8.4, thus yielding the sodium salt of chloroacetic acid (sodium chloroacetate) in situ. An aqueous solution of copper sulfate was added dropwise until 0.01 moles had been added, thus yielding the metal-chloroacetate compound in situ. Trimethylamine solution (25%, aqueous) was added until a total of 0.01 moles had been added. The solution was allowed to stir for about 15 to about 30 minutes at 25° C., thus yielding a betaine-metal complex as the final product.

In view of the above disclosure, one of skill in the art should appreciate that one illustrative embodiment of the present invention includes a method of making a betaine transition metal complex. Such an illustrative method may include the steps of: a) reacting a solution including an alkali metal salt of chloroacetic acid with a solution including the transition metal salt to give a solution including a chloroacetate transition metal complex; and b) reacting the solution including the chloroacetate transition metal complex with trimethylamine to give a solution including the betaine transition metal complex. The illustrative method may be carried out such that reacting chloroacetic acid with a neutralizing amount of alkali metal hydroxide to give the alkali metal salt of chloroacetic acid generates the alkali metal salt of chloroacetic acid.

In one preferred embodiment of the illustrative method, the transition metal salt is selected from zinc salts, copper salts, iron salts, chromium salts, manganese salts, cobalt salts, their hydrates and mixtures of these salts, and in a more preferred illustrative method the transition metal salt is selected from zinc halide salts, zinc sulfate salts, zinc nitrate salts, copper halide, copper sulfate copper nitrate, iron halide, iron sulfate, iron nitrate, chromium halide, chromium sulfate, chromium nitrate, manganese halide, manganese sulfate, manganese nitrate, cobalt halide, cobalt sulfate, cobalt nitrate, the hydrates of these salts and the mixture of these salts. In another illustrative embodiment, the transition metal salt is a zinc salt, and preferably the zinc salt is selected from zinc chloride, zinc bromide, zinc sulfate, zinc nitrate, their hydrates and combinations of these. The reactions of the present illustrative method may take place in any suitable solvent, but preferably the reactions take place in an aqueous solvent. The illustrative method may further include the step of stripping any excess trimethylamine from the solution including the betaine transition metal complex. The isolation of the betaine transition metal complex may also be included as a step in the illustrative embodiment in which case the process would include the step of isolating the betaine transition metal complex by precipitation or evaporative reduction of the solution including the betaine transition metal complex. The product of the illustrative method is a betaine transition metal complex having the general formula

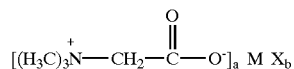

wherein a is a whole number from 1upto and including 6; M is a transition metal ion selected from zinc, copper, iron, chromium, manganese cobalt and mixtures thereof; X is a counter ion and b is a whole integer selected to electrostatically balance the charge of the complex salt. Preferably the transition metal ion M is zinc and the counter ion X is a halide, sulfate or other similar suitable counter ion. As indicated the value of a may have a value from 1 upto and including 6, but preferably the value of a is 2 to 4.

The scope of the present disclosure should be understood to also include a transition metal betaine complex salt having the formula

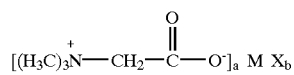

wherein a is a value between 1 and 6; M is a transition metal ion selected from zinc, copper, iron, chromium, manganese cobalt and mixtures thereof; X is a counter ion and b is a whole integer selected to electrostatically balance the charge of the complex salt. Within such an illustrative embodiment, it is preferred that the counter ion X is selected from halide, sulfate, nitrate and mixtures thereof Further the transition metal ion may be selected from zinc (II), copper (II), copper (I), iron (II), iron (III), cobalt (II), cobalt (III), chromium (II), chromium (III), manganese (II) manganese (III), and mixtures of these. Preferably the transition metal ion M is zinc and the counter ion X is a halide, sulfate or other similar suitable counter ion. As indicated the value of a may have a value from 1 upto and including 6, but preferably the value of a is 2 to 4. The illustrative transition metal-betaine complex is preferably the product of the process including the steps: a) reacting a solution including an alkali metal salt of chloroacetic acid with a solution including the transition metal salt to give a solution including a chloroacetate transition metal complex; and b) reacting the solution including the chloroacetate transition metal complex with trimethylamine to give a solution including the betaine transition metal complex. The method may further include the step of stripping any excess trimethylamine from the solution including the betaine transition metal complex. The isolation of the betaine transition metal complex may also be included as a step in which case the process would include the step of isolating the betaine transition metal complex by precipitation or evaporative reduction of the solution including the betaine transition metal complex.

Another illustrative embodiment of the present invention is a trace metal feed supplement comprising an effective amount of a transition metal betaine complex having the general formula:

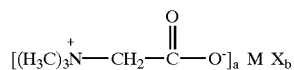

wherein a is a value between 1 and 6; M is a transition metal ion selected from zinc, copper, iron, chromium, manganese cobalt and mixtures thereof; X is a counter ion and b is a whole integer selected to electrostatically balance the charge of the complex salt. Within such an illustrative embodiment, it is preferred that the counter ion X is selected from halide, sulfate, nitrate and mixtures thereof. Further the transition metal ion may be selected from zinc (II), copper (II), copper (I), iron (II), iron (III), cobalt (II), cobalt (III), chromium (II), chromium (III), manganese (II) manganese (III), and mixtures of these. Preferably the transition metal ion M is zinc and the counter ion X is a halide, sulfate or other similar suitable counter ion. As indicated the value of a may have a value from 1 upto and including 6, but preferably the value of a is 2 to 4. The transition metal-betaine complex is preferably the product of the process including the steps: a) reacting a solution including an alkali metal salt of chloroacetic acid with a solution including the transition metal salt to give a solution including a chloroacetate transition metal complex; and b) reacting the solution including the chloroacetate transition metal complex with trimethylamine to give a solution including the betaine transition metal complex. The method may further include the step of stripping any excess trimethylamine from the solution including the betaine transition metal complex. The isolation of the betaine transition metal complex may also be included as a step in which case the process would include the step of isolating the betaine transition metal complex by precipitation or evaporative reduction of the solution including the betaine transition metal complex. The illustrative trace metal feed supplement may be delivered as a solution, preferably an aqueous solution, or it may be delivered in solid form. The solid form may include a carrier such as animal feed, rice hulls, or other suitable carrier for feed supplements.

One of skill in the art should also appreciate that the present invention also includes a method for providing a trace metal-betaine feed supplement to an animal. Such an illustrative method includes the steps: a) mixing a suitable animal feed mixture with an effective amount of a trace metal betaine complex, and b) providing said supplemented feed mixture to the animal for consumption by the animal. It is preferred within such illustrative method that the trace metal-betaine complexes have the general formula

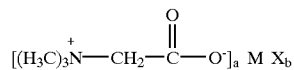

wherein a is a whole number between 1 and 6; M is a transition metal ion selected from zinc, copper, iron, chromium, manganese cobalt and mixtures thereof; X is a counter ion and b is a whole integer selected to electrostatically balance the charge of the complex salt. Within such an illustrative embodiment, it is preferred that the counter ion X is selected from halide, sulfate, nitrate and mixtures thereof. Further the transition metal ion may be selected from zinc (II), copper (II), copper (I), iron (II), iron (III), cobalt (II), cobalt (III), chromium (II), chromium (III), manganese (II) manganese (III), and mixtures of these. Preferably the transition metal ion M is zinc and the counter ion X is a halide, sulfate or other similar suitable counter ion. As indicated the value of a may have a value from 1 upto and including 6, but preferably the value of a is 2 to 4. It is more preferred that the trace metal-betaine complex is the product of the process including the steps: a) reacting a solution including an alkali metal salt of chloroacetic acid with a solution including the transition metal salt to give a solution including a chloroacetate transition metal complex; and b) reacting the solution including the chloroacetate transition metal complex with trimethylamine to give a solution including the betaine transition metal complex. The method may further include the step of stripping any excess trimethylamine from the solution including the betaine transition metal complex. The isolation of the betaine transition metal complex may also be included as a step in which case the process would include the step of isolating the betaine transition metal complex by precipitation or evaporative reduction of the solution including the betaine transition metal complex.

A further illustrative aspect of the present invention is an animal feed composition that includes: an effective amount of a trace metal betaine complex salt having the formula

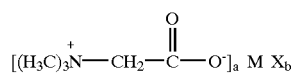

wherein a is a whole number between 1 and 6; M is a transition metal ion selected from zinc, copper, iron, chromium, manganese cobalt and mixtures thereof; X is a counter ion and b is a whole integer selected to electrostatically balance the charge of the complex salt, and a suitable animal feed mixture for said animal. Preferably within such illustrative embodiment, the transition metal ion is selected from zinc (II), copper (II), copper (I), iron (II), iron (III), cobalt (II), cobalt (III), chromium (II), chromium (III), manganese (II) manganese (III), and mixtures of these and the counter ion X is selected from halide, sulfate, nitrate and mixtures thereof. It is more preferred that the trace metal-betaine complex salt is the product of the process including the steps: a) reacting a solution including an alkali metal salt of chloroacetic acid with a solution including the transition metal salt to give a solution including a chloroacetate transition metal complex; and b) reacting the solution including the chloroacetate transition metal complex with trimethylamine to give a solution including the betaine transition metal complex. The process utilized to make the trace metal betaine complex may further include the step of stripping any excess trimethylamine from the solution including the betaine transition metal complex. The isolation of the betaine transition metal complex may also be included as a step in which case the process would include the step of isolating the betaine transition metal complex by precipitation or evaporative reduction of the solution including the betaine transition metal complex.

The present invention also should be understood to include a method of making animal feed composition. Such a method may include the step of mixing an effective amount of a trace metal betaine complex salt having the formula

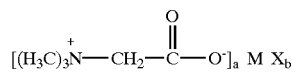

wherein a is a whole number between 1 and 6; M is a transition metal ion selected from zinc, copper, iron, chromium, manganese cobalt and mixtures thereof; X is a counter ion and b is a whole integer selected to electrostatically balance the charge of the complex salt, with a suitable animal feed mixture for said animal to form said animal feed mixture. It is preferred that the transition metal ion is selected from zinc (II), copper (II), copper (I), iron (II), iron (III), cobalt (II), cobalt (III), chromium (II), chromium (III), manganese (II) manganese (III), and mixtures of these and the counter ion X is selected from halide, sulfate, nitrate and mixtures thereof. It is more preferred that the trace metal-betaine complex salt is the product of the process including the steps of: a) reacting a solution including an alkali metal salt of chloroacetic acid with a solution including the transition metal salt to give a solution including a chloroacetate transition metal complex; and b) reacting the solution including the chloroacetate transition metal complex with trimethylamine to give a solution including the betaine transition metal complex. The process utilized to make the trace metal betaine complex may further include the step of stripping any excess trimethylamine from the solution including the betaine transition metal complex. The isolation of the betaine transition metal complex may also be included as a step in which case the process would include the step of isolating the betaine transition metal complex by precipitation or evaporative reduction of the solution including the betaine transition metal complex.

While the compositions and methods of this invention have been described in terms of preferred embodiments, it will be apparent to those of skill in the art that variations may be applied to the process described herein without departing from the concept and scope of the invention. All such similar substitutes and modifications apparent to those skilled in the art are deemed to be within the scope and concept of the invention as it is set out in the following claims.

What is claimed is:

1. A method of making a betaine transition metal complex, the method comprising a) reacting a solution including an alkali metal salt of chloroacetic acid with a solution including the transition metal salt to give a solution including a chloroacetate transition metal complex; and b) reacting the solution including the chloroacetate transition metal complex with trimethylamine to give a solution including the betaine transition metal complex.

2. The method of claim 1 wherein the alkali metal salt of chloroacetic acid is generated by reacting chloroacetic acid with a neutralizing amount of alkali metal hydroxide to give the alkali metal salt of chloroacetic acid.

3. The method of claim 1 wherein the transition metal salt is selected from zinc salts, copper salts, iron salts, chromium salts, manganese salts, cobalt salts, their hydrates and mixtures of these salts.

4. The method of claim 1 wherein the transition metal salt is selected from zinc halide salts, zinc sulfate salts, zinc nitrate salts, copper halide, copper sulfate copper nitrate, iron halide, iron sulfate, iron nitrate, chromium halide, chromium sulfate, chromium nitrate, manganese halide, manganese sulfate, manganese nitrate, cobalt halide, cobalt sulfate, cobalt nitrate, the hydrates of these salts and the mixture of these salts.

5. The method of claim 1 wherein the transition metal salt is a zinc salt.

6. The method of claim 1 wherein the transition metal salt is selected from zinc chloride, zinc bromide, zinc sulfate, zinc nitrate, their hydrates and combinations of these.

7. The method of claim 1 wherein the reactions take place in an aqueous solvent.

8. The method of claim 1 further comprising stripping any excess trimethylamine from the solution including the betaine transition metal complex.

9. The method of claim 8 further comprising isolating the betaine transition metal complex by precipitation or evaporative reduction of the solution including the betaine transition metal complex.

10. The method of claim 1 wherein said betaine transition metal complex has the general formula

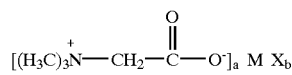

wherein a is a whole number between 1 and 6; M is a transition metal ion selected from zinc, copper, iron, chromium, manganese cobalt and mixtures thereof; X is a counter ion and b is a whole integer selected to electrostatically balance the charge of the complex salt.

11. A trace metal feed supplement comprising an effective amount of a compound having the general formula:

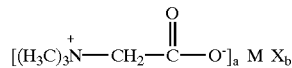

wherein a is a whole number between 1 and 6; M is a transition metal ion selected from zinc, copper, iron, chromium, manganese cobalt and mixtures thereof; X is a counter ion and b is a whole integer selected to electrostatically balance the charge of the complex salt.

12. The composition of claim 11 wherein the counter ion X is selected from halide, sulfate, nitrate and mixtures thereof.

13. The composition of claim 12 wherein the transition metal ion is selected from zinc (II), copper (II), copper (I), iron (II), iron (III), cobalt (II), cobalt (III), chromium (II), chromium (III), manganese (II) manganese (III), and mixtures of these.

14. The composition of claim 13 wherein the trace metal-feed supplement is the product of the process comprising
   a) reacting a solution including an alkali metal salt of chloroacetic acid with a solution including the transition metal salt to give a solution including a chloroacetate transition metal complex; and
   b) reacting the solution including the chloroacetate transition metal complex with trimethylamine to give a solution including the betaine transition metal complex.

15. A method of providing a trace metal-betaine feed supplement to an animal, said method comprising
   a) mixing a suitable animal feed mixture with an effective amount of a trace metal betaine complex,
   b) providing said supplemented feed mixture to the animal for consumption by the animal.

16. The method of claim 15 wherein said trace metal-betaine complex has the general formula

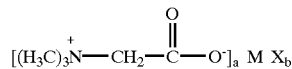

wherein a is a whole number between 1 and 6; M is a transition metal ion selected from zinc, copper, iron, chromium, manganese cobalt and mixtures thereof; X is a counter ion and b is a whole integer selected to electrostatically balance the charge of the complex salt.

17. The method of claim 15 wherein the trace metal-betaine complex is the product of the process comprising
   a) reacting a solution including an alkali metal salt of chloroacetic acid with a solution including the transition metal salt to give a solution including a chloroacetate transition metal complex; and
   b) reacting the solution including the chloroacetate transition metal complex with trimethylamine to give a solution including the betaine transition metal complex.

18. An animal feed composition comprising
   an effective amount of a trace metal betaine complex salt having the formula

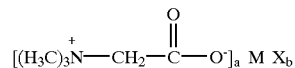

wherein a is a whole number between 1 and 6; M is a transition metal ion selected from 11 zinc, copper, iron, chromium, manganese cobalt and mixtures thereof; X is a counter ion and b is a whole integer selected to electrostatically balance the charge of the complex salt, and a suitable animal feed mixture for said animal.

19. The composition of claim 18 wherein the counter ion X is selected from halide, sulfate, nitrate and mixtures thereof.

20. The composition of claim 18 wherein the transition metal ion is selected from zinc (II), copper (II), copper (I), iron (II), iron (III), cobalt (II), cobalt (III), chromium (II), chromium (III), manganese (II) manganese (III), and mixtures of these.

21. The composition of claim 18 wherein the trace metal-betaine complex salt is the product of the process comprising
   a) reacting a solution including an alkali metal salt of chloroacetic acid with a solution including the transition metal salt to give a solution including a chloroacetate transition metal complex; and
   b) reacting the solution including the chloroacetate transition metal complex with trimethylamine to give a solution including the betaine transition metal complex.

22. A method of making an animal feed composition, said method comprising
   mixing an effective amount of a trace metal betaine complex salt having the formula

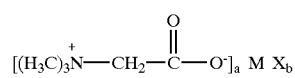

wherein a is a whole number between 1 and 6; M is a transition metal ion selected from zinc, copper, iron, chromium, manganese cobalt and mixtures thereof; X is a counter ion and b is a whole integer selected to electrostatically balance the charge of the complex salt, and a suitable animal feed mixture for said animal to form said animal feed mixture.

23. The composition of claim 22 wherein the counter ion X is selected from: halide, sulfate, nitrate and mixtures thereof.

24. The composition of claim 22 wherein the transition metal ion is selected from zinc (II), copper (II), copper (I), iron (II), iron (III), cobalt (II), cobalt (III), chromium (II), chromium (III), manganese (II) manganese (III), and mixtures of these.

25. The composition of claim 22 wherein the trace metal-betaine complex salt is the product of the process comprising
   a) reacting a solution including an alkali metal salt of chloroacetic acid with a solution including the transition metal salt to give a solution including a chloroacetate transition metal complex; and
   b) reacting the solution including the chloroacetate transition metal complex with trimethylamine to give a solution including the betaine transition metal complex.

* * * * *

UNITED STATES PATENT AND TRADEMARK OFFICE
CERTIFICATE OF CORRECTION

PATENT NO. : 6,579,904 B1 Page 1 of 1
DATED : June 17, 2003
INVENTOR(S) : Harvey B. H It is certified that error appears in the above-identified patent and that said Letters Patent is hereby corrected as shown below:

Column 12,
Line 10, delete "11"

Signed and Sealed this

Seventh Day of October, 2003

JAMES E. ROGAN
*Director of the United States Patent and Trademark Office*